United States Patent [19]

Helmlinger et al.

[11] Patent Number: 4,634,548

[45] Date of Patent: Jan. 6, 1987

[54] NOVEL BICYCLIC EPOXIDES AND COMPOSITIONS

[75] Inventors: Daniel Helmlinger, Gockhausen; Mario Pesaro, Zurich, both of Switzerland

[73] Assignee: Givaudan Corporation, Clifton, N.J.

[21] Appl. No.: 569,020

[22] Filed: Jan. 9, 1984

[30] Foreign Application Priority Data

Jan. 13, 1983 [CH] Switzerland ............................ 158/83

[51] Int. Cl.$^4$ ............................ A61K 7/46; C11B 9/00
[52] U.S. Cl. ................................ 252/522 R; 426/536; 549/545
[58] Field of Search .................... 252/522 R; 549/545; 426/536

[56] References Cited

U.S. PATENT DOCUMENTS

| 3,773,836 | 11/1973 | Hall | 549/545 X |
| 3,898,289 | 8/1975 | Schneider | 549/545 X |
| 3,927,083 | 12/1975 | Hall et al. | 549/545 X |
| 3,932,516 | 1/1976 | Shaffer et al. | 549/545 X |
| 4,267,373 | 5/1981 | Hauck et al. | 549/545 X |

OTHER PUBLICATIONS

E. T. Theimer, "Fragrance Chemistry, the Science of the Sense of Smell", 1982, Academic Press, New York, NY Chap 14, pp. 514–524.
Ibid. Chap. 15, pp. 551–554.

Primary Examiner—Helen M. S. Sneed
Attorney, Agent, or Firm—Robert F. Tavares

[57] ABSTRACT

The invention is concerned with novel bicyclic epoxides, a process for their manufacture and novel fragrance and flavor compositions containing the same.

17 Claims, No Drawings

NOVEL BICYCLIC EPOXIDES AND COMPOSITIONS

THE INVENTION

The invention is concerned with novel bicyclic epoxides of the formula

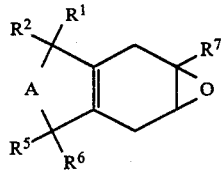

wherein:

A represents:

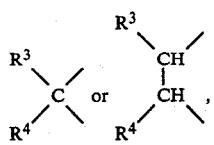

$R^1$, $R^2$, $R^5$ and $R^6$ represent hydrogen, methyl, ethyl or isopropyl provided that $R^1$, $R^2$, $R^5$ and $R^6$ are not alike unless they are methyl, and $R^3$, $R^4$ and $R^7$ represent hydrogen or methyl.

Formula I includes epoxides having the octahydronaphthalene structure (Ia) and those having the tetrahydroindane structure (Ib):

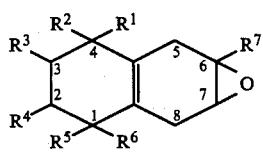

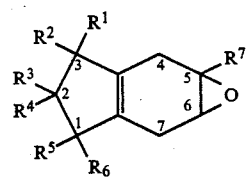

The invention is also concerned with novel fragrance and flavor compositions containing epoxides of formula I and a process for the manufacture of said epoxides.

DESCRIPTION OF THE PREFERRED EMBODIMENTS

The compounds of formula I can be prepared by a process which comprises epoxidizing a bicyclic 1,4-cyclohexadiene of the formula

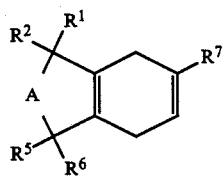

wherein A and $R^1$ to $R^7$ have the same significance as in formula I. Preferred methods which can be used to convert the compounds of formula II to epoxides include the following:

(1) Converting the bicyclic 1,4-cyclohexadienes of formula II to α-halohydrins of the formula

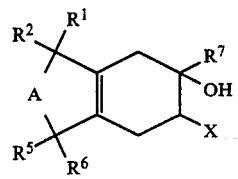

wherein A and $R^1$ to $R^7$ have the same significance as in formula I and X signifies chlorine, bromine or iodine, and then converting said α-halohydrin to the corresponding epoxide of formula I. This can be done, for example, by the addition of a hypohalous acid HOX to the tri- or disubstituted double bond of a bicyclic 1,4-cyclohexadiene of formula II [see Houben-Weyl, "Methoden der Organischen Chemie", Volue VI, 1a, Part 1 (1979) page 564] followed by dehydrohalogenation of the resulting α-halohydrin of formula III by treatment with a base (see, for example, "Organic Functional Group Preparations" S. R. Sandler and W. Karo, Acad. Press 1968, p. 109 and "Organic Reactions in Steroid Chemistry" Vol. II, Ed, J. Fried and J. A. Edwards, Van Nostrand Reinhold Co., 1972, p. 15).

(2) Treatment of a bicyclic 1,4-cyclohexadiene of forumla II with an organic peracid such as, for example, peracetic acid or perbenzoic acid in an inert solvent such as, for example, dichloromethane (see "Oxidation in Organic Chemistry" Ed. W. S. Trahanovsky, Part C, Acad. Press 1978, p. 225).

(3) Treatment of a bicyclic 1,4-cyclohexadiene of formula II with an alkyl hydroperoxide such as, for example, tert-butyl hydroperoxide or ethylbenzene hydroperoxide in the presence of a metal catalyst such as, for example, a molybdenum or vanadium compound. The reaction is conveniently carried out in an inert solvent such as, for example, benzene or 1,2-dichloroethane at temperatures between 80° C. and 120° C. (see "Metal Catalyzed Oxidations of Organic Compounds", R. A. Sheldon and J. K. Kochi, Acad. Press 1981, p. 275).

The above epoxidation methods also yield, in addition to compounds of formula I, an epoxide which results from epoxidation at the tetrasubstituted, bridgehead double bond. This isomeric epoxide has the formula

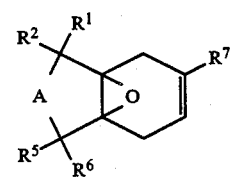

wherein A and $R^1$ to $R^7$ have the same significance as defined previously. The ratio of epoxides I/IV depends on the structure of the bicyclic 1,4-cyclohexadiene of formula II and on the epoxidation method used. The epoxidation with an alkyl hydroperoxide/metal catalyst (method 3) which is very regioselective and yields predominately the epoxides of formula I, is the preferred epoxidation method.

Depending on the nature of the substituents $R^1$ to $R^7$, the compounds of formula I can be obtained according to the process provided by the invention as mixtures of diastereomers or mixtures of structural isomers. The separation of these mixtures into the individual components can be carried out, for example, by gas chromatography or column chromatography. However, on economical grounds it is preferable to use the mixtures.

The starting material for the above epoxidation methods, namely the 1,4-cyclohexadienes of formula II, may be prepared by reduction of the corresponding benzene derivative of the formula

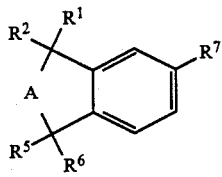

V wherein A and $R^1$ to $R^7$ have the same significance as defined previously. Reduction methods generally known in the art may be used, such as for example, those of Birch or Benkeser or electrochemical methods, using metal cathodes (see Houben-Weyl, "Methoden der Organischen Chemie", Volume V, 1(1972) p. 613).

The reduction according to Birch can be carried out utilizing alkali or alkaline earth metals at low temperature (e.g., $-78°$ C. to $-33°$ C.) in liquid ammonia which contains as an additive an alcohol such as, for example, ethanol. The reduction according to Benkeser can be carried out utilizing alkali or alkaline earth metals in alkylamines, for example, methylamine, ethylamine, ethylenediamine, etc., in the presence of an alcohol such as ethanol, isopropanol, isoamyl alcohol, etc. Sodium and lithium are especially suitable metals for use in the reductions. An addition of diethyl ether or tetrahydrofuran promotes the solubility of the benzene derivative of formula V.

These reductions often produce, as byproducts, isomeric bicyclic cyclohexadiene compounds of the formula

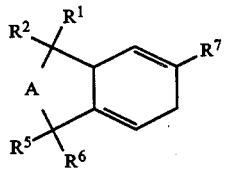

VI and bicyclic cyclohexene derivatives of the formula

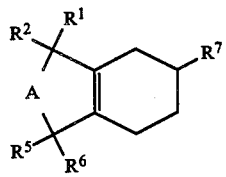

VII wherein A and $R^1$ to $R^7$ are as previously defined.

These byproducts are practically unaffected by the epoxidation in accordance with the invention and can be separated from the epoxides of formula I by distillation.

The compounds of formula I have organoleptic properties which make them particularly suitable for use as odorants and flavorants. They are characterized by powerful, diffusive and very natural-warm top notes in the direction of musk, with fruity and woody olfactory aspects. In addition, a powdery-flowery bottom tone is worthy of mention. Therefore, the compounds of formula I constitute, inter alia, a novel group of musk odorant substances, the bycyclic hydrocarbon structure of which carries a 1,2-epoxy grouping (oxirane) as the characteristic feature in place of the acetyl group bonded to a benzene ring hitherto known in bicyclic systems. Preferred compounds of formula I are 6,7-epoxy-1,1,4,4,6-pentamethyl-1,2,3,4,5,6,7,8-octa-hydronaphthalene; 6,7-epoxy-1,1,3,4,4,6-hexamethyl-1,2,3,4,5,6,7,8-octa-hydronaphthalene and 5,6-epoxy-1,1,2,3,3-pentamethyl-4,5,6,7-tetrahydroindane.

On the basis of their natural odour notes the compounds of formula I are especially suitable for modifying known compositions.

The compounds of formula I combine with numerous known odorant substance ingredients of natural or synthetic origin, whereby the range of natural ingredients can embrace not only readily-volatile but also semi-volatile and difficulty-volatile components and that of the synthetic ingredients can embrace representatives from practically all classes of substances, as will be evident from the following compilation:

Natural products such as tree moss absolute, basil oil, tropical fruit oils (such as bergamot oil, mandarin oil, etc.), mastix absolute, myrtle oil, palmarosa oil, patchouli oil, petitgrain oil Paraguay, wormwood oil;

alcohols such as geraniol, linalool, nerol, phenylethyl alcohol, rhodinol, cinnamic alcohol;

aldehydes such as citral, Helional ™, α-hexylcinnamaldehyde, hydroxycitronellal, Lilial ® (p-tert.butyl-α-methyl-dihydrocinnamaldehyde), methylnonylacetaldehyde;

ketones such as allylionone, α-ionone, β-ionone, methylionone;

esters such as allyl phenoxyacetate, benzyl salicylate, cinnamyl propionate, dimethylbenzylcarbinyl butyrate, ethyl acetoacetate, linalyl acetate, methyl dihydrojasmonate, styrallyl acetate, vetiveryl acetate;

lactones such as γ-undecalactone;

various additional components often used in perfumery such as musk ketone, indole, p-methane-8-thiol-3-one, methyleugenol.

In addition, the manner in which the compounds of formula I round-off and harmonize, but without dominating, the odour notes of known compositions is remarkable. Thus, for example, in perfume bases with tea and green character they underline the soft and flowery note, and in rose bases the sought after character of the heavy and sweet Bulgarian rose is underlined.

In fruit bases the compounds of formula I can be used effectively to produce a velvety-soft, natural-sweet and rounded-off effect in the direction of peach and apricot.

The compounds of formula I (or mixtures thereof) can be used in wide limits which, for example, can extend in compositions from 0.1% (detergents) to 30% (alcoholic solutions). It will be appreciated that these values are not limiting values, since the experienced perfumer can also produce effects with even lower concentrations or can synthesize novel complexes with even higher concentrations. The preferred concentrations range between 0.5% and 25%. The compositions manufactured with compounds of formula I can be used for all kinds of perfumed consumer goods (eaux de cologne, eaux de toilette, essences, lotions, creams, shampoos, soaps, salves, powders, toothpastes, mouth washes, deodorants, detergents, tobacco etc).

The compounds of formula I can accordingly be used in the manufacture of compositions and, as will be evident from the above compilation, a wide range of known odorant substances or odorant substance mixtures can be used. In the manufacture of such compositions that known odorant substances specified above can be used according to methods which are known to the perfumer such as, for example, according to W. A. Poucher, Perfumes, Cosmetics, Soaps 2, 7th Edition, Chapman and Hall, London 1974.

The new compounds of formula I are also excellently suited for use in fruit flavours of the widest variety of types, but especially also for the flavouring of tobacco.

As flavouring substances the compounds of formula I can be used, for example, for the production or improvement, intensification, enhancement or modification of fruit flavours of the widest variety of types (e.g. blackberry or apricot flavours). As fields of use for these flavours there come into consideration, for example, foodstuffs (yoghurt, confectionery etc), semi-luxury consumables (tea, tobacco etc) and drinks (lemonades etc).

The pronounced flavour qualities of the compounds of formula I enable them to be used as flavouring substances in low concentrations. A suitable concentration embraces, for example, the range of 0.01 ppm–100 ppm, preferably 0.01 ppm–20 ppm, in the finished product, i.e. the flavoured foodstuff, semi-luxury consumable or drink.

In the flavouring of, for example, tobacco the concentration can, however, also be higher and can embrace a wider range, for example the range of 1 to 1000 ppm, preferably 50 to 500 ppm.

The compounds of formula I can be mixed with ingredients used for flavouring substance compositions or added to such flavourants in the usual manner. Under the flavourants used in accordance with the invention there are to be understood flavouring substance compositions which can be diluted or dispersed in edible materials in a manner known per se. They contain, for example, about 0.1–10 wt.%, especially 0.5–3 wt.% of compounds of formula I. They can be converted according to methods known per se into the usual forms of use such as solutions, pastes or powders. The products can be spray-dried, vacuum-dried or lyophilized.

The known flavouring substances conveniently used in the manufacture of such flavourants are either contained in the above compilation or can be taken from the respective literature; see, for example, J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc. Cleveland, Ohio 1975.

For the manufacture of the usual forms of use there come into consideration, for example, the following carrier materials, thickening agents, flavour improvers, spices and adjuvant ingredients etc.:

Gum arabic, tragacanth, salts or brewers' yeast, alginates, carragene or similar absorbents; indoles, maltol, dienals, spice oleoresins, smoke flavours; cloves, diacetyl, sodium citrate; monosodium glutamate, disodium inosine-5′-monophosphate (IMP), disodium guanosine-5-phosphate (GMP); or special flavouring substances, water, ethanol, propylene glycol, glycerine.

EXAMPLES

The following examples illustrate the present invention:

Example 1

Method A 0.544 g of a hydrocarbon mixture containing about 37.5% (according to GC) of 1,1,4,4,6-pentylmethyl-1,2,3,4,5,8-hexahydronaphthalene (Lb IIa) are dissolved in 8 ml of acetone and treated with a solution of 0.25 g of sodium dihydrogen phosphate monohydrate in 1 ml of water. Thereto there is added a solution of 0.132 g of 65% calcium hypochlorite in 1 ml of water and after stirring for 30 minutes, a further 0.25 g of sodium dihydrogen phosphate monohydrate and 0.132 g of 65% calcium hypochlorite in 1 ml of water. After stirring for 1.5 hours, the mixture is extracted with dichloromethane and the organic phase is washed with sodium chloride solution. After removal of the solvent, there is obtained 0.54 g of crude product. After distilling off the unreacted hydrocarbon, there are obtained 0.082 g (32% yield based on IIa) of 7-chloro-6-hydroxy-1,1,4,4,6-pentamethyl-1,2,3,4,5,6,7,8-octahydronaphthalene which, after recrystallization from hexane, melts at 122°–124° C.

0.3 g of the above chlorohydrin are treated with 6 ml of a 1N methanolic potassium hydroxide solution and stirred at room temperature for 30 minutes. Thereupon, the mixture is extracted with hexane and the extract is washed neutral with water. After removal of the solvent by concentration, there are obtained 0.24 g of an oil which is distilled at 85° C./0.05 Torr in a bulb-tube. There is obtained 0.19 g (75% yield) of 6,7-epoxy-1,1,4,4,6-pentamethyl-1,2,3,4,5,6,7,8-octahydronaphthalene (Ia). $n_D^{20}=1.4973$;

$^1$H-HMR (400 mHz, CDCL$_3$): δ (ppm) 0.95 (s, 6H); 0.98 (s, 6H; 1.37 (s, 3H); 3.08 (m, 1H); MS (m/e): 220 (M+), 205, 187, 177, 161, 147, 121, 105.

Method B 0.742 g of a hydrocarbon mixture containing about 27.5% (according to GC) of 1,1,4,4,6-pentamethyl-1,2,3,4,5,8-hexahydronaphthalene (IIa) and 0.01 g of sodium acetate are treated with 3 ml of dichloromethane. At 10° C. there is added a solution of 0.215 ml of 40% peracetic acid and 0.01 g of sodium acetate in 0.5 ml of dichloromethane and the mixture is stirred at room temperature for 2.5 hours. Thereupon, there are added 0.2 ml of a saturated sodium hydrogen sulphite solution and 0.8 ml of water and the mixture is stirred for 2.5 hours. The mixture is extracted with dichloromethane and the extract is washed neutral with sodium hydrogen carbonate solution and water. After drying and removing the solvent, there are obtained 0.65 g of an oil which is separated into its components by preparative thick-layer chromatography (Merck silica gel plates, running agent (2x): dichloromethane). From the layer with Rf=0.58 there is isolated 0.018 g of 4a,8a-epoxy-1,1,4,4-6-pentamethyl-1,2,3,4,4a,5,8,8a-octahydronaphthalene (IVa).

¹H-NMR (400 mHz, CDCl₃): δ (ppm) 1.01 (s, 3H); 1.02 (s, 3H); 1.03 (s, 3H); 1.05 (s, 3H); 1.63 (s, 3H); 5.16 (m, 1H) MS (m/e): 220 (M+), 205, 187, 177, 151, 121, 109 107.

Odour: berry-like and mint-like; delicate(weak).

The layer with Rf=0.47 yields 0.068 g of 6,7-epoxy-1,1,4,4,6-pentamethyl-1,2,3,4,5,6,7,8-octahydronaphthalene (Ia).

Method C 200.7 g of a hydrocarbon mixture containing about 62.6% (according to GC) of 1,1,4,4,6-pentamethyl-1,2,3,4,5,8-hexahydronaphthalene (IIa) are dissolved in 590 ml of 1,2-dichloroethane and treated at 20° C. with 1.62 g of molybdenum hexacarbonyl and 0.62 g of anhydrous disodium hydrogen phosphate. The mixture is heated to 75°–80° C. (internal temperature) and there are added dropwise without further heat input within 20 minutes 324 ml of an about 2.85 molar anhydrous solution of tert.butyl hydroperoxide in 1,2-dichloroethane. The mixture is held at reflux for 3.5 hours, thereafter cooled to 5° C., 210 ml of 20% sodium sulphite solution are added within 20 minutes and the mixture is stirred vigorously for a further 2.5 hours. The mixture is extracted with dichloromethane and the extract is washed neutral with water. After drying and removal of the solvent by concentration, there are obtained 208.6 g of a yellow oil. This is distilled in a high vacuum over a Widmer column. The fraction boiling at 72°–80° C./0.02 Torr (88.2 g; 65% yield based on IIa) represents 6,7-epoxy-1,1,4,4,6-pentamethyl-1,2,3,4,5,6,7,8-octahydronaphthalene (Ia).

$n_D^{20} = 1.4960$.

Odour: musk-like, reminiscent of ambrette seeds, fruity.

D. Preparation of the starting material

The hydrocarbon mixture is prepared as follows:

160 ml of methylamine are placed at −15° C. in a suitable reaction vessel and treated with 40 g of 1,1,4,4,6-pentamethyl-1,2,3,4-tetrahydronaphthalene (Va) and with 18 g of ethanol. 2.7 g of lithium are added portionwise to this solution at −15° C. After the disappearance of the lithium (about 10 minutes), there are added a further 9 g of ethanol and subsequently 1.4 g of lithium. After a further 15 minutes, the lithium has completely reacted and the methylamine is distilled off. The residue is extracted with hexane, the extract is washed neutral with water and dried. After removing the solvent, 40 g of crude product are obtained. This contains the following substances (area percentages according to GC in parentheses; isolation by preparative gas chromatography):

IIa: (55%) ¹H-NMR (400 mHz, CDCl₃): δ (ppm) 0.99 (s, 6H); 1.01 (s, 6H); 1.68 (m, 3H); 5.42 (m, 1H); MS (m/e): 204 (M+), 189, 133, 119, 105.

VIa: (7%) ¹H-NMR (400 mHz, CDCl₃): δ (ppm) 0.63 (s, 3H); 0.99 (s, 3H); 1.03 (s, 3H); 1.07 (s, 3H); 1.69 (s, 3H); 5.43 (m, 1H); 5.50 (t, 1H); MS (m/e): 204 (M+), 189, 135, 133, 119, 105.

VIIa: (30%) ¹H-NMR (400 mHz, CDCl₃): δ (ppm) 0.93 (d, 3H); 0.93 (s, 6H); 0.96 (s, 6H); MS (m/e): 206 (M+), 191, 162, 150, 135, 121, 109.

Example 2

108.5 g of a hydrocarbon mixture containing about 57.6% (according to GC) of 1,1,3,4,4,6-hexamethyl-1,2,3,4,5,8-hexahydronaphthalene (IIb) are dissolved in 236 ml of 1,2-dichloroethane and treated in accordance with method C described in Example 1 with 0.755 g of molybdenum hexacarbonyl, 0.286 g of disodium hydrogen phosphate and 150.5 ml of 2.85 molar tert.butyl hydroperoxide solution. After working-up and high vacuum distillation, there is obtained a fraction boiling at 68°–79° C./0.02 Torr (47.2 g; 70.5% yield based on IIb). This fraction consists of a diastereomer mixture of 6,7-epoxy-1,1,3,4,4,6-hexamethyl-1,2,3,4,5,6,7,8-octahydronaphthalene and 5,6-epoxy-1,1,3,4,4,6-hexamethyl-1,2,3,4,4a,5,6,7-octahydronaphthalene in the ratio of about 92:8 and exhibits the following data:

$n_D^{20} = 1.4986$;

¹H-NMR (400 mHz, CDCl₃): δ (ppm) 0.77+0.80 (2s, 3H); 0.85+0.86 (2d, 3H); 0.92+0.94 (2s, 3H); 0.97 (s, 3H); 0.99 (s, 3H); 1.37+1.375 (2s, 3H); 3.08 (m, about 1H); 3.14 (m, about 0.1H); 5.23 (m, about 0.1H);

MS (m/e): 234 (M+), 219, 201, 191, 175, 161, 149, 135, 121, 107.

Odour: musk-like and pear-like.

Component (IIb) can be isolated pure from the hydrocarbon mixture used by repeated recrystallization from hexane and can subsequently be epoxidized in accordance with method C of Example 1. The thus-obtained 6,7-epoxide (diastereomer mixture about 1:1 according to NMR) exhibits the following data:

¹H-NMR (400 mHz, CDCl₃): δ (ppm 0.77+0.80 (2s, 3H); 0.85+0.86 (2d, 3H); 0.92+0.94 (2s, 3H); 0.97 (s, 3H); 0.99 (s, 3H); 1.37+1.375 (2s, 3H); 3.08 (m, 1H);

MS (m/e): 234 (M+), 219, 201, 191, 175, 161, 149, 135, 121, 107.

Odour: musk-like.

Further, component (VIb) can be separated by preparative gas chromatography from the hydrocarbon mixture used and can subsequently be epoxidized in accordance with method C of Example 1. The thus-obtained 5,6-epoxide exhibits the following data:

¹H-NMR (400 mHz, CDCl₃): δ (ppm) 0.57 (s, 3H); 0.79 (d, 3H); 1.02 (s, 3H); 1.04 (s, 3H); 1.16 (s, 3H); 1.35 (s, 3H); 3.14 (m, 1H); 5.23 (m, 1H);

MS (m/e): 234 (M+), 216, 201, 191, 159, 145, 135, 121, 109.

Odour: fruity, slightly woody, slightly musk-like, delicate.

Preparation of the starting material

The above hydrocarbon mixture is prepared as follows analogously to the preparation described in Example 1 for the starting material therein: 172.8 g of 1,1,3,4,4,6-hexamethyl-1,2,3,4-tetrahydronaphthalene are dissolved at −15° C. in 1.15 l of methylamine and 80 ml of tetrahydrofuran and reacted with a total of 228 ml of ethanol and 27 g of lithium (in each case in four portions). After working-up, there are obtained 179 g of crude product which is composed of the following substances (area percentages according to GC in parenthesis; isolation by preparative gas chromatography):

Isomer IIb: (61.5%) ¹H-NMR (400 mHz, CDCl₃): δ (ppm) 0.83 (s, 3H); 0.88 (d, 3H); 0.96 (s, 3H); 1.00 (s, 3H); 1.02 (s, 3H); 1.69 (s, 3H); 5.42 (m, 1H); MS (m/e): 218 (M+), 203, 175, 159, 147, 133, 119, 105; m.p. 46°–48° C.

Isomer VIb: (4.9%) ¹H-NMR (400 mHz, CDCl₃): δ (ppm) 0.47 (s, 3H); 0.78 (d, 3H); 0.99 (s, 3H); 1.05 (s, 3H); 10.6 (s, 3H); 1.70 (s, 3H); 5.49 (m, 2H).

6,7-Dihydro-IIb (=VIIb) (32.5%) ¹H-NMR (360 mHz, CDCl₃): δ (ppm) 0.77 (d, 3H); 0.85 (2d, 3H); 0.88 to 1.0 (7s, 12H); MS (m/e): 220 (M+), 205, 191, 177, 163, 149, 135, 121, 109.

Example 3

44.5 g of a hydrocarbon mixture containing (according to GC) about 85.4% of 1,1,3,3,5-pentamethyl-4,7-dihydroindane (IIc) are dissolved in 200 ml of 1,2-dichloroethane and treated in accordance with method C described in Example 1 with 0.53 g of molybdenum hexacarbonyl, 0.2 g of disodium hydrogen phosphate and 140 ml of 2.85 molar tert.butyl hydroperoxide solution. After working-up and high vacuum distillation, there are obtained 23.6 g (corresponding to 57.2% yield based on IIc) of 5,6-epoxy-1,1,3,3,5-pentamethyl-4,5,6,7-tetrahydroindane with the following data:

$n_D^{20} = 1.4790$;

$^1$H-NMR (400 mHz, CDCl$_3$): δ (ppm) 1.00 (s, 12H); 1.41 (s, 3H); 3.13 (m, 1H);

MS (m/e): 206 (M+), 191, 173, 163, 147, 133, 121, 107, 105.

Odour: musk-like and dried fruit-like, cedarwood-like, fruity.

Preparation of the starting material

The above hydrocarbon mixture is prepared as follows analogously to the preparation described in Example 1 for the starting material therein: 56.4 g of 1,1,3,3,5-pentamethyl-indane are dissolved at −15° C. in 240 ml of methylamine and reacted with a total of 36.3 ml of ethanol and 6.08 g of lithium (in each case in two portions). After working-up, there are obtained 56.3 g of crude product which is composed of the following substances (area percentages according to GC in parenthesis; isolated by preparative gas chromatography):

IIc: (85.4%) $^1$H-NMR (360 mHz, CDCl$_3$): δ (ppm) 1.03 (s, 6H); 1.05 (s, 6H); 1.74 (s, 3H); 5.49 (m, 1H) MS (m/e): 190 (M+), 175, 159, 145, 133, 119, 105.

5,6-Dihydro-IIc (=VIIc): (11.6%) MS (m/e): 192 (M+), 177, 149, 135, 121, 107.

Example 4

21.2 g of a hydrocarbon mixture containing (according to GC) about 51.5% of 1,1,2,3,3,5-hexamethyl-4,7-dihydroindane (IId) and 25.7% of 3-ethyl-1,1,3,5-tetramethyl-4,7-dihydroindane (IIe) are dissolved in 80 ml of 1,2-dichloroethane and treated in accordance with method C described in Example 1 with 0.212 g of molybdenum hexacarbonyl, 0.08 g of disodium hydrogen phosphate and 56 ml of 2.85 molar tert.butyl hydroperoxide solution. After working-up and high vacuum distillation, there is obtained a fraction boiling at 71°–75° C./0.02 Torr (10.25 g; 58.2% yield based on IId+IIe). In accordance with capillary GC this contains three isomeric epoxides in the ratio: 43%:33%:24%. This epoxide mixture exhibits the following data:

$n_D^{20} = 1.4870$;

MS (m/e): 220 (M+), 205, 191, 161, 147, 135, 121, 105.

Odour: musk-like, woody.

The three peaks visible in the capillary GC are subsequently separated by preparative gas chromatography and the thus-obtained pure substances are analyzed. The main product (peak 1) is one of the diastereomeric 5,6-epoxy-1,1,2,3,3,5-hexamethyl-4,5,6,7-tetrahydroindanes with the following data:

$^1$H-NMR (400 mHz, CDCl$_3$): δ (ppm) 0.82 (2s, 6H); 0.85 (d, 3H); 0.93 (2s, 6H); 1.42 (s, 3H); 3.15 (m, 1H);

MS (m/e): 220 (M+), 205, 191, 177, 161, 147, 135, 121, 118, 105.

Odour: musk-like and dried fruit-like, slightly woody.

Peak 2 is the second diastereomeric 5,6-epoxy-1,1,2,3,3,5-hexamethyl-4,5,6,7-tetrahydroindane with the following data:

$^1$H-NMR (400 mHz, CDCl$_3$): δ (ppm) 0.79 (s, 6H); 0.86 (d, 3H); 0.92 (2s, 6H); 1.41 (s, 3H); 3.12 (m, 1H);

MS (m/e): 220 (M+), 205, 191, 177, 161, 147, 135, 121, 107, 105.

Odour: woody, slightly musk-like.

Peak 3 is the non-separated pair of diastereomers (about 1:1 according to NMR) of 5,6-epoxy-3-ethyl-1,1,3,5-tetramethyl-4,5,6,7-tetrahydroindane with the following data:

$^1$H-NMR (400 mHz, CDCl$_3$): δ (ppm) 0.73+0.76 (2t, 3H); 0.97 to 1.02 (5s, 9H); 1.40 (s, 3H); 3.12 (m, 1H);

MS (m/e): 220 (M+), 205, 191, 173, 161, 147, 133, 121, 107, 105.

Odour: dried fruit-like, slightly musk-like.

Preparation of the starting material

The hydrocarbon mixture used in this Example is prepared as follows analogously to the preparation described in Example 1 for the starting material therein: 223 g of a mixture consisting of about 70% of 1,1,2,3,3,5-hexamethylindane and about 30% of 3-ethyl-1,1,3,5-tetramethylindane are dissolved at −15° C. in 700 ml of methylamine and reacted with a total of 151.8 g of ethanol and 22.9 g of lithium (in each case in two portions). After working-up, there are obtained 245 g of crude product which is composed of the following substances (area percentages according to GC in parentheses; isolated by preparative gas chromatography):

Isomer IId: (63.0%) $^1$H-NMR (400 mHz, CDCl$_3$): δ (ppm) 0.84 (s, 3H); 0.86 (s, 3H); 0.89 (d, 3H); 0.95 (s, 3H); 0.97 (s, 3H); 1.73 (s, 3H); 5.48 (m, 1H); MS (m/e): 204 (M+), 189, 147, 133, 119, 107.

Isomer IIe: (20.2%) $^1$H-NMR (400 mHz, CDCl$_3$): δ (ppm) 0.78 (t, 3H); 1.01 (s, 3H); 1.02 (s, 3H); 1.04 (s, 3H); 1.73 (s, 3H); 5.48 (m, 1H); MS (m/e): 204 (M+), 189, 175, 133, 119, 105.

5,6-Dihydro-IId (=VIId): (9.7%) MS (m/e) 206 (M+), 191, 149, 135, 121, 107.

5,6-Dihydro-IIe (=VIIe): (3.5%) MS (m/e) 206 (M+), 191, 177, 149, 135, 121, 107.

Example 5

35.8 g of a hydrocarbon mixture containing (according to GC) about 64.3% of 1-isopropyl-2,3,3,5-tetramethyl-4,7-dihydroindane (IIf) are dissolved in 105 ml of 1,2-dichloroethane and treated in accordance with method C described in Example 1 with 0.29 g of molybdenum hexacarbonyl, 0.11 g of disodium hydrogen phosphate and 57.2 ml of 2.85 molar tert.butyl hydroperoxide solution. After working-up and high vacuum distillation, there is obtained a fraction boiling at 64°–71° C./0.05 Torr (13.9 g=54% yield based on IIf) consisting of 5,6-epoxy-1-isopropyl-2,3,3,5-tetramethyl-4,5,6,7-tetrahydroindane with the following data:

$n_D^{20} = 1.4899$;

$^1$H-NMR (400 mHz, CDCl$_3$): δ (ppm) 0.74 (d, 3H); 0.79+0.83 (2d, 3H); 0.92 to 0.94 (m, 9H); 1.39+1.40 (2s, 3H); 3.08+3.09 (2m, 1H);

MS (m/e): 234 (M+), 219, 205, 191, 173, 159, 147, 133, 121, 105.

Odour: musk-like, fruity.

Preparation of the starting material

The hydrocarbon mixture used in this Example is prepared as follows analogously to the preparation described in Example 1 for the starting material therein: 37.5 g of 1-isopropyl-2,3,3,5-tetramethyl-indane (Vf) are dissolved at −15° C. in 140 ml of methylamine and reacted with a total of 34.5 ml of ethanol and 4.08 g of lithium (in each case in three portions). After working-up, there are obtained 32.7 g of crude product which is composed of the following main components (area percentages according to GC in parentheses; isolated by preparative gas chromatography):

Isomer IIf: (64.3%) $^1$H-NMR (400 mHz, CDCl$_3$): δ (ppm) 0.79 (s, 3H); 0.84 (d, 3H); 0.93 (d, 3H); 0.96 (d, 3H); 0.96 (s, 3H); 1.72 (s, 3H); 5.43 (m, 1H); MS (m/e): 218 (M+), 203, 175, 159, 147, 133, 119, 105.

5,6-Dihydro-IIf (=VIIf): (14.3%) MS (m/e): 220 (M+), 205, 177, 163, 149, 135, 121, 107.

Example 6

19.1 g of a hydrocarbon mixture containing (according to GC) about 76.9% of 1-isopropyl-2,2,3,3,5-pentamethyl-4,7-dihydroindane (IIg) are dissolved in 61 ml of 1,2-dichloroethane and treated in accordance with method C described in Example 1 with 0.167 g of molybdenum hexacarbonyl, 0.064 g of disodium hydrogen phosphate and 37.3 ml of 2.85 molar tert.butyl hydroperoxide solution. After working-up and high vacuum distillation, there is obtained a fraction boiling at 70°–74° C./0.07 Torr (5.8 g; 37% yield based on 17a) consisting of 5,6-epoxy-1-isopropyl-2,2,3,3,5-pentamethyl-4,5,6,7-tetrahydroindane with the following data:

$n_D^{20}$=1.4975;

$^1$H-NMR (400 mHz, CDCl$_3$): δ (ppm) 0.73+0.75+0.78+0.79+0.80 (5s, 9H); 0.88 (2s, 3H); 0.95 (2d, 3H); 1.01+1.03 (2d, 3H); 1.39+1.41 (2s, 3H); 3.08 (m, 1H);

MS (m/e): 248 (M+), 233, 205, 187, 177, 161, 145, 135, 121, 109, 105.

Odour: delicate musk-like.

Preparation of the starting material

The hydrocarbon mixture used in this Example is prepared analogously to the preparation described in Example 1 for the starting material therein: 20.0 g of 1-isopropyl-2,2,3,3,5-pentamethyl-indane are dissolved at −15° C. in 71 ml of methylamine and reacted with a total of 20.2 ml of ethanol and 2.4 g of lithium (in each case in three portions). After working-up, there are obtained 19.1 g of crude product which contains the following main substances (area percentages according to GC in parentheses; isolated by preparative gas chromatography):

Isomer IIg: (76.8%) $^1$H-NMR (400 mHz, CDCl$_3$): δ (ppm) 0.80+0.81+0.83+0.92 (4s, 12H); 0.96 (d, 3H); 1.03 (d, 3H); 1.73 (s, 3H); 5.44 (m, 1H); MS (m/e): 232 (M+), 217, 189, 175, 159, 147, 133, 119, 105.

5,6-Dihydro-IIg (=VIIg) (13.2%) MS (m/e): 234 (M+), 219, 191, 177, 163, 149, 135, 121, 107.

Example 7

35 g of a hydrocarbon mixture containing (according to GC) 43% of 1,1,4,4-tetramethyl-1,2,3,4,5,8-hexahydronaphthalene (IIh) are dissolved in 140 ml of 1,2-dichloroethane and treated in accordance with method C described in Example 1 with 0.304 g of molybdenum hexacarbonyl, 0.1148 g of disodium hydrogen phosphate and 65 ml of 2.85 molar tert.butyl hydroperoxide solution. After working-up, 30 g of crude product are obtained. 10 g thereof are chromatographed on 600 g of silica gel Merck (0.04–0.063 mm) (elution agent: 2–3% ether/hexane). 1.9 g of 6,7-epoxy-1,1,4,4-tetramethyl-1,2,3,4,5,6,7,8-octahydro-naphthalene are obtained.

$^1$H-NMR (CDCl$_3$ 400 mHz): 0.95 (s, 6H); 0.98 (s, 6H); 1.45 (m, 4H); 2.31 (d, J=18, 2H); 2.61 (d, J=18, 2H); 3.26 (s, 2H);

MS (m/e) 206 (M+ 49) 191 (76); 173 (21); 147 (100); 133 (23); 107 (21); 91 (10); 60 (2).

Odour: musk-like, fruity (similar to thibetolide).

The hydrocarbon mixture required for this reaction is prepared as follows analogously to the preparation described in Example 1 for the starting material therein: 205 g of 1,1,4,4-tetramethyl-1,2,3,4-tetrahydronaphthalene are dissolved at −15° C. in 800 ml of methylamine and reacted with two portions of ethanol (101.2 g and 50.6 g) and two portions of lithium (15.3 g and 7.6 g). After working-up, there are obtained 198 g of crude product which is composed of the following main components (area percentages according to GC; isolated by preparative gas chromatography):

31% of 1,1,4,4-tetramethyl-1,2,3,4,5,6,7,8-octahydro naphthalene,

50% of 1,1,4,4-tetramethyl-1,2,3,4,5,8-hexahydronaphthalene (IIh).

$^1$H-NMR (CDCl$_3$) 400 mHz): 0.99 (s, 12H); 1.5 (s, 4H); 2.64 (d, J=1.8, 4H); 5.72 (s, broad, 2H);

MS: 190 M+, 175, 119, 105, 91.

Example 8

6.1 g of a hydrocarbon mixture containing (according to GC) 59% of 1,1,2,3,3-pentamethyl-4,7-dihydroindane (IIj) are dissolved in 15 ml of 1,2-dichloroethane and treated in accordance with Example 1, method C, with 53 mg of molybdenum hexacarbonyl, 20 mg of disodium hydrogen phosphate and 11.4 ml of 2.85 molar tert.butyl hydroperoxide solution. After working-up, 4 g of crude product are obtained. By chromatography over 300 g of silica gel Merk (0.04–0.063 mm) there are isolated the following individual compounds:

Cis- or trans-5,6-epoxy-1,1,2,3,3-pentamethyl-4,5,6,7-tetrahydroindane (isomer A)

$^1$H-NMR (CDCl$_3$ 400 mHz) 0.79 (s, 6H); 0.85 (d, J=7 Hz 3H); 0.92 (s, 6H); 1.47 (q, J=7 Hz, 1H); 2.3 (d, broad J=16 Hz, 2H); 2.45 (d, broad, J=16 Hz, 2H); 3.3 s, broad, 2H);

MS 206, 191, 177, 145, 135, 121, 105, 91, 65, 41.

Cis or trans 5,6-epoxy-1,1,2,3,3-pentamethyl-4,5,6,7-tetrahydroindane (isomer B)

$^1$H-NMR (CDCl$_3$ 400 mHz) 0.81 (s, 6H); 0.84 (d, J=7 Hz, 3H); 0.92 (s, 6H; 1.54 (q, J=7 Hz, 1H); 2.27 (d, broad, J=15 Hz, 2H); 2.53 (d, broad, J=15 Hz, 2H); 3.33 (s broad, 2H);

MS M+ 206, 191, 173, 147, 135, 121, 107, 105, 91, 87, 65, 55, 41.

Odour of the mixture of compounds: musk-like, slightly fruity, woody.

The hydrocarbon mixture required as the starting material is prepared as follows analogously to the preparation described in Example 1 for the starting material therein: 207 g of a mixture of 1,1,2,3,3-pentamethylindane (75%) and 3-ethyl-1,1,3-trimethylindane (17%) are dissolved at −15° in 700 ml of methylamine and reacted with two portions of ethanol (101 g and 50 g) and two portions of lithium (15.3 g and 7.6 g). After working-up, there are obtained 221 g of product which is composed of the following substances (area percentages according to GC; isolated by preparative gas chromatography):

59% of 1,1,2,3,3-pentamethyl-4,7-dihydroindane (IIj)

$^1$H-NMR (CDCl$_3$ 400 mHz) 0.84 (s, 6H); 0.88 (d, J=7 Hz, 3H); 0.95 (s, 6H); 1.55 (q, J=7 Hz, 1H); 2.61 (m, 4H); 5.77 (m, 2H);

MS 190 M+, 175, 147, 133, 119, 105, 91, 69, 55, 41.

12% of 3-ethyl-1,1,3-trimethyl-4,7-dihydroindane (IIk)

$^1$H-NMR (CDCl$_3$ 400 mHz) 0.77 (t, J=7 Hz, 3H); 1.01 (s, 6H); 1.05 (s, 3H); 1.32 (m, J=7 Hz, 2H); 1.45 (d, J=13 Hz, 1H); 1.7 (d, J=13 Hz, 1H); 2.56 (m, 4H), 5.77 (m, 2H);

MS 190, 175, 161, 145, 133, 119, 105, 91, 79.

20% of 1,1,2,3,3-pentamethyl-4,5,6,7-tetrahydroindane (5,6-dihydro-IIj).

Example 9

81 g of a hydrocarbon mixture containing (according to GC) 69% of 3-ethyl-1,1,3-trimethyl-4,7-dihydroindane (IIk) are dissolved in 600 ml of 1,2-dichloroethane and treated in accordance with Example 1, method C, with 795 mg of molybdenum hexacarbonyl, 300 mg of disodium hydrogen phosphate and 180 ml of 2.85 molar tert.butyl hydroperoxide solution. After working-up, there are obtained 90 g of crude product which contains (according to GC) 61% of a mixture of cis- and trans-5,6-epoxy-3-ethyl-1,1,3-trimethyl-4,5,6,7-tetrahydroindane.

Spectral data of the (cis and trans) mixture:

$^1$H-NMR: 0.74 (3H, t, J=8 Hz); 0.76 (3H, t, J=8 Hz); 0.795 (3H, s); 0.985 (3H, s); 0.985 (3H, s); 0.99 (3H, s); 1.01 (3H, s); 1.015 (3H, s); 3.3 (2H, m); 3.3 (2H, m);

MS: 206 M+, 191, 177, 169, 147, 133.

Odour: damascone-like, fruity, woody, delicately (slightly) musk-like

The hydrocarbon mixture required as the starting material is prepared as follows analogously to the preparation described in Example 1 for the starting material therein: 86 g of 3-ethyl-1,1,3-trimethylindane are dissolved in 600 ml of methylamine and reacted at −15° C. with two portions of ethanol (44 g and 22 g) and two portions of lithium (6.3 g and 3.15 g). After working-up, there are obtained 83 g of product which is composed of the following substances (area percentages according to GC; isolated by preparative gas chromatography):

69% of 3-ethyl-1,1,3-trimethyl-4,7-dihydroindane (IIk)

$^1$H-NMR (CDCl$_3$) 400 mHz): 0.775 (3H, t, J=8 Hz); 1.017 (6H, s); 1.05 (3H, s); 2.56 (4H, m); 5.775 (2H, m);

MS: 190 M+, 175, 161, 145, 133, 131, 119, 105.

16% of 3-ethyl-1,1,3-trimethyl-4,5,6,7-tetrahydroindane.

Example 10

8 g of a hydrocarbon mixture containing (according to GC) 54% of 1,1,3,4,4-pentamethyl-1,2,3,4,5,8-hexahydronaphthalene (II 1) are dissolved in 40 ml of dichloroethane and treated in accordance with Example 1, method C, with 57 mg of molybdenum hexacarbonyl, 21.6 mg of disodium hydrogen phosphate and 12.31 ml of 2.85 molar tert.butyl hydroperoxide solution. After working-up, 9.7 g of crude product are obtained. By chromatography there is obtained a mixture of cis- and trans-6,7-epoxy-1,1,3,4,4-pentamethyl-1,2,3,4,5,6,7,8-octahydronaphthalene.

Spectral data of the cis/trans mixture:

$^1$H-NMR: (CDCl$_3$, 400 mHz): 0.775 (3H, s); 0.795 (3H, s); 0.850 (3H, d, J=7); 0.860 (3H, d, J=7); 0.930 (3H, s); 0.945 (3H, s); 0.972 (3H, s); 0.987 (3H, s); 0.99 (3H, s); 3.27 2H, m); 3.27 (2H, m);

MS: 220 M+, 205, 187, 161, 147, 135, 121, 107, 91, 79, 69.

Odour: very strongly musk-like, powdery, sweet.

The hydrocarbon mixture required as the starting material is prepared as follows analogously to the preparation described in Example 1 for the starting material therein: 8.6 g of 1,1,3,4,4-pentamethyl-1,2,3,4-tetrahydronaphthalene are dissolved at −15° C. in 150 ml of methylamine and reacted with two portions of ethanol (3.92 g and 1.95 g) and two portions of lithium (570 mg and 293 mg). After working-up, there are obtained 8.4 g of crude product which is composed of the following substances (area percentages, isolated by preparative gas chromatography).

54% of 1,1,3,4,4-pentamethyl-1,2,3,4,5,8-hexahydronaphthalene $^1$H-NMR (CDCl$_3$ 400 mHz): 0.802 (3H, s); 0.88 (3H, d, J=7 Hz); 0.967 (3H, s); 0.98 (3H, s); 1.02 (3H, s); 5.735 (2H, m);

MS: 204 M+ 189, 167, 145, 135, 119, 105, 91, 83.

43% of 1,1,3,4,4-pentamethyl-1,2,3,4,5,6,7,8-octahydronaphthalene $^1$H-NMR (CDCl$_3$ 400 mHz): 0.78 (3H, s); 0.85 (3H, d, J=8 Hz); 0.915 (3H, s); 0.925 (3H, s); 0.98 (3H, s);

MS: 206, 191, 175, 161, 149, 135, 123, 109.

Example 11

137 g of a hydrocarbon mixture containing (according to GC) 40% of a mixture of 1-ethyl-1,4,4,6-tetramethyl-1,2,3,4,5,8-hexahydronaphthalene (IIm) and 1-ethyl-1,4,4,7-tetramethyl-1,2,3,4,5,8-hexahydronaphthalene (IIn) are dissolved in 400 ml of dichloroethane and treated in accordance with Example 1, method C, with 1 g of molybdenum hexacarbonyl, 0.35 g of disodium hydrogen phosphate and 175 ml of 2.85 molar tert.butyl hydroperoxide solution. After working-up, 152 g of crude product are obtained. By chromatography there is obtained a mixture of 6,7-epoxy-1-ethyl-1,4,4,6-tetramethyl-1,2,3,4,5,6,7,8-octahydronaphthalene (cis and trans) and 6,7-epoxy-1-ethyl-1,4,4,7-tetramethyl-1,2,3,4,5,6,7,8-octahydronaphthalene (cis and trans).

$^1$H-NMR (CDCl$_3$ 400 mHz): 0.75 (3H, t, J=7 Hz); 0.940 (3H, s); 0.945 (3H, s); 0.985 (3H, s); 0.99 (3H, s); 1.357 (3H, s); 1.37 (3H, s); 3.075 (1H, m);

MS: 234 M+, 205, 191, 177, 161, 141, 135.

Odour: musk-like, balsamic, reminiscent of pine and blackberries.

The hydrocarbon mixture required as the starting material is prepared as follows analogously to the preparation described in Example 1 for the starting material therein: 237 g of a mixture of 1-ethyl-1,4,4,6-tetramethyl-1,2,3,4,-tetrahydronaphthalene and 1-ethyl-1,4,4,7-tetramethyl-1,2,3,4-tetrahydronaphthalene are dissolved in 700 ml of methylamine and reacted at −15° C. with three portions of ethanol (93 g, 47 g 47 g) and three portions of lithium (15.2 g, 7.6 g, 7.6 g). After working-up, there are obtained 233 g of material which is composed of the following substances (area percentages, isolated by preparative gas chromatography):

40% of a mixture of 1-ethyl-1,4,4,6-tetramethyl-1,2,3,4,5,8-hexahydronaphthalene (IIm) and 1-ethyl-1,4,4,7-tetramethyl-1,2,3,4,5,8-hexahydronaphthalene (IIn).

¹H-NMR (CDCl₃ 400 mHz): 0.737 (3H, t, J=7 Hz); 0.747 (3H, t, J=7 Hz); 0.955 (3H, s); 0.975 (3H, s); 0.982 (3H, s); 0.990 (3H, s); 1,002 (3H, s); 1.007 (3H, s); 1.68 (3H, s, broad); 1.68 (3H, s, broad); 5.42 (1H, m); 5.42 (1H, m);

MS: M+ 218, 203, 189, 175, 173, 159, 147, 133, 119, 105, 91, 77, 69.

45% of a mixture of cis- and trans-1-ethyl-1,4,4,6-tetramethyl-1,2,3,4,5,6,7,8-octahydronaphthalene (dihydro-IIm=VIIm) and 1-ethyl-1,4,4,7-tetramethyl-1,2,3,4,5,6,7,8-octahydronaphthalene (dihydro-IIn=VIIn)

¹H-NMR (CDCl₃ 400 mHz): 0.892 (s); 0.905 (s); 0.925 (s); 0.945 (s); 0.950 (s); 0.950 (s); 0.965 (s);

MS: M+ 220, 205, 191, 177, 149, 135, 121, 109, 105, 95.

Preparation of the tetrahydronaphthalene 210 g of 2,5-dimethyl-hept-1-en-5-ol are dissolved in 469 g of concentrated hydrochloric acid. The mixture is heated to 50° C. and 397 g of sulphuric acid are added dropwise within 30 minutes while stirring. The mixture is stirred for a further 30 minutes, then diluted with ether, washed neutral with water and evaporated. 243 g of 2,5-dimethyl-2,5-dichloroheptane are obtained in this manner.

. A solution of 240 g of 2,5-dichloro-2,5-dimethylheptane in 340 ml of toluene is added dropwise within 1 hour to a suspension of 20.8 g of aluminium chloride in 333 g of toluene. The mixture is stirred for 50 minutes, a further 15 g of aluminium chloride are added, the mixture is left to react for 10 minutes, poured on to ice and extracted with hexane. The organic phase is washed with water, dried over sodium sulphate and evaporated. There are obtained 274 g of crude product which represents a mixture (91%) of the following compounds:

1-Ethyl-1,4,4,6-tetramethyl-1,2,3,4-tetrahydronaphthalene, 1-ethyl-1,4,4,7-tetramethyl-1,2,3,4-tetrahydronaphthalene, Spectral data of the mixture:

¹H-NMR (CDCl₃ 400 mHz): 0.767 (3H, t, J=7 Hz); 0.775 (3H, t, J=7 Hz); 1.207 (3H, s); 1,217 (3H, s); 1.232 (3H, s); 1,242 (3H, s); 1,272 (3H, s); 1.282 (3H, s); 2.290 (3H, s); 2,297 (3H, s); 6.94 (1H, d, J=8 Hz; 6.94 (1H, d, J=8 Hz); 7.02 (1H, s, broad); 7.105 (1H, s); 7.11 (1H, d, J=8 Hz); 7.2 (1H, d, J=8 Hz);

MS: M+ 216, 187, 173, 157, 155, 145, 131, 115, 105, 91.

Example 12

105 g of a hydrocarbon mixture containing (according to GC) 56% of 1-isopropyl-4,4,7-trimethyl-1,2,3,4,5,8-hexahydronaphthalene (IIo) are dissolved in 400 ml of dichloroethane and treated in accordance with Example 1, method C, with 1.1 g of molybdenum hexacarbonyl, 0.4 g of disodium hydrogen phosphate and 228 ml of a 2.8 molar tert.butyl hydroperoxide solution. After working-up, 115 g of crude product are obtained. By chromatography there is obtained pure 6,7-epoxy-1-isopropyl-4,4,7-trimethyl1,2,3,4,5,6,7,8-octahydronaphthalene.

¹H-NMR (CCl₄ 400 mHz): 0.695 (3H, d, J=7 Hz); 0.920 (3H, s); 0.937 (3H, d, J=5 Hz); 0.99 (3H, s); 1.282 (3H, s); 2.875 (1H, m);

MS: 234 M+, 191, 178, 173, 103, 147, 133, 119, 105, 91, 77, 91, 77.

Odour: musk, peppery, spicy.

The hydrocarbon mixture required as the starting material is prepared as follows analogously to the method described in Example 1 for the starting material therein: 190 g of 1-isopropyl-4,4,7-trimethyl-1,2,3,4-tetrahydronaphthalene (purity 75%) are dissolved in 650 ml of methylamine and reacted at −15° C. with two portions of ethanol (80 g and 40 g) and two portions of lithium (12.2 g and 6 g). After working-up, there are obtained 180 g of product which is composed of the following main components (area percentages according to GC; isolated by preparative gas chromatography):

56 g of 1-isopropyl-4,4,7-trimethyl-1,2,3,4,5,8-hexahydronaphthalene (IIo)

¹H-NMR CDCl₃ 400 mHz): 0.71 (3H, d, J=7 Hz); 0.945 (3H, d, J=7 Hz); 0.975 (3H, s); 0.98 (3H, s); 1.665 (3H, s broad); 5.435 (1H, m);

MS: 218 M+, 203, 175, 159, 145, 133, 119, 105, 91.

20% of 1-isopropyl-4,4,7-trimethyl-1,2,3,4,5,6,7,8-octahydronaphthalene (dihydro-IIO=VIIo)

¹H-NMR (CDCl₃ 400 mHz): 0.67 (3H, d, J=7 Hz); 0.905 (3H, d, J=7 Hz); 0.937 (3H, s); 0.945 (3H, s);

MS: 220, 205, 177, 162, 149, 135, 121, 106, 95.

Preparation of the tetrahydronaphthalene 1050 g of sulphuric acid are provided and a mixture of 1.5 l of toluene and 497 g of 2,6-dimethyl-hept-5-en-2-ol are added dropwise during 35 minutes while cooling (10° C.). The mixture is stirred at room temperature for 1.5 hours. The mixture is now diluted with hexane, poured on to ice, washed neutral, dried and evaporated. After distillation there are obtained 455 g of 1-isopropyl-4,4,7-trimethyl-1,2,3,4-tetrahydro-naphthalene (purity 75%).

In Examples 13A–13J hereinafter the numerals given after the notation "epoxide" denotes the number of the respective Examples hereinbefore. The preferred compounds are "epoxide 1", "epoxide 2" and "epoxide 8", i.e. the novel epoxides 6,7-epoxy-1,1,4,4,6-pentamethyl-1,2,3,4,5,6,7,8-octahydronaphthalene, 6,7-epoxy-1,1,3,4,4,6-hexamethyl-1,2,3,4,5,6,7,8-octahydronaphthalene and 5,6-epoxy-1,1,2,3,3-pentamethyl-4,5,6,7-tetrahydroindane referred to in Examples 1, 2 and 8, respectively.

Example 13

A. Perfumery base in the direction of cologne.

| | Parts by weight |
|---|---|
| Myrascone ™ Givaudan (2-ethyl-3,6,6-trimethyl-2-cyclohexene-1-carboxylic acid ethyl ester) | 160 |
| Hydroxycitronellal | 120 |
| Madrox ™ Givaudan (1-methyl-1-methoxy-cyclododecane) | 120 |
| Sandela ® Givaudan (3-isocamphyl-(5)-cyclohexanol) | 120 |
| Bergamot oil | 120 |
| Pine needle oil | 60 |
| Musk ketone | 60 |
| Givescone ™ Givaudan (2-ethyl-6,6-dimethyl-2-cyclohexene-1-carboxylic acid ethyl ester) | 60 |
| Petitgrain oil (synthetic) | 40 |
| Corps Cassis ™ Givaudan (p-methane-8-thiol-3-one) | 10 |
| Tree moss extract | 10 |
| Dipropylene glycol (DPG) | 80 |
| | 960 |

If 40 parts of epoxide 4 are added to this cologne base, then it becomes much more herby and fresher. Thus, it is well suited for men's colognes.

On the other hand, the addition of 40 parts of epoxide 2 brings a very fine musk character to the cologne.

By the addition of 40 parts of epoxide 1, the cologne base becomes much more alive (lively) and flowery. The resulting composition is suitable for a woman's cologne.

B. Perfumery base in the direction of tea.

|  | Parts by weight |
| --- | --- |
| Linalyl acetate | 200 |
| Linalool | 120 |
| Hydroxycitronellal | 120 |
| Madrox TM Givaudan | 120 |
| Methyl dihydrojasmonate | 80 |
| Patchouli leaf oil | 60 |
| Methyleugenol | 40 |
| Acetanisole (p-methoxyacetophenone) | 40 |
| Basil oil | 20 |
| Bornyl acetate | 20 |
| Tree moss absolute | 20 |
| Dipropylene glycol | 130 |
|  | 970 |

If 30 parts of epoxide 1 are added to this aromatic base, then it immediately becomes much more herby, fresher and substantially more powerful.

The addition of 30 parts of epoxide 4 produces a rather flowery version of the tea base.

C. Perfumery base in the direction of melon.

|  | Parts by weight |
| --- | --- |
| Myraldylacetat | 140 |
| Hexenyl salicylate | 80 |
| Methyl dihydrojasmonate | 60 |
| Ethyl acetoacetate | 60 |
| Cyclamen aldehyde | 50 |
| Verdyl Acetat ® (dihydro-nor-dicyclo-pentadienyl acetate) | 50 |
| Lilial ® Givaudan (p-tert.butyl-α-methyl-hydrocinnamaldehyde) | 10 |
| Rhodinol | 10 |
| Eugenol | 5 |
| Maltyl isobutyrate (10% in DPG) | 5 |
| Acetanisole | 5 |
| Cis-6-nonenol (10% in DPG) | 5 |
| Dipropylene glycol | 510 |
|  | 990 |

If 10 parts of epoxide 1 are added to this fruity base (with melon character), then it becomes more fruity and sweeter. The melon character is greatly reduced and there now results a herby-flowery effect which confers an exotic fruit note to the base. On the other hand, if 30 parts of epoxide 5 are added, then the base becomes more fruity, more juicy and more natural.

D. Perfumery base in the direction of rose.

|  | Parts by weight |
| --- | --- |
| Phenylethyl alcohol | 460 |
| Dipropylene glycol | 260 |
| Geraniol | 80 |
| Cinnamic alcohol substitute (synthetic) | 70 |
| Nerol | 60 |
| Cinnamyl propionate | 50 |
|  | 980 |

If 20 parts of epoxide 3 are added to this base which has a generally rosy character, then it becomes rounded-off very finely and an impression of much more typical rose note results. In particular, the base becomes much more harmonic and has more volume.

On the other hand, if 20 parts of epoxide 2 are added, then the rosy character is almost completely lost and the very pleasant musk character now dominates. The very simply produced base is just like a finished composition.

If 20 parts of epoxide 5 are added to the base, then there results a fruity-velvety effect in the direction of the sought after tea rose.

E. Fruity perfumery base.

|  | Parts by weight |
| --- | --- |
| Dipropylene glycol | 710 |
| α-Ionone | 160 |
| Dimethylbenzylcarbinyl butyrate | 100 |
| α-Allylionone | 80 |
| Fructone ® IFF (2-methyl-1,3-dioxolan-2-ethyl acetate) | 60 |
| Palmarosa oil | 40 |
| γ-Undecalaconte | 30 |
| Synthetic osmanthus oil substitute | 10 |
|  | 950 |

If 50 parts of epoxide 3 are added to this fruity base, then a pronounced apricot-peach note appears strongly in the foreground. The addition of 50 parts of epoxide brings about a musk effect which fits very well into this fruity note. Also, the addition of 50 parts of epoxide 4 produces a musk note. By the addition of 50 parts of epoxide 1 the base immediately becomes much softer and is now especially suitable for the perfuming of cosmetics.

F. Perfumery base in the direction of tobacco.

|  | Parts by weight |
| --- | --- |
| o-tert. butylcyclohexyl acetate | 400 |
| Jasmine oil (synthetic) | 300 |
| Musk ketone | 40 |
| Sandela ® | 40 |
| Styrallyl acetate | 30 |
| Coumarin | 20 |
| Isobutylquinoline (10% in DPG) | 10 |
| Lavender oil | 10 |
| Vetiver oil | 10 |
| Galbanum oil | 10 |
| Vassura oil | 10 |
| Dipropylene glycol | 40 |
|  | 920 |

Here, the addition of 80 parts of epoxide 7 produces an attractive musk effect, thus obtainable in a cheaper manner.

G. Perfumery base in the direction of rose.

|  | Parts by weight |
| --- | --- |
| Phenylethyl alcohol | 300 |
| Geraniol | 250 |
| Jasmine "lavage" (aqueous distillate) | 200 |
| Citronellol extra | 100 |
| α-Ionone | 40 |
| $C_{10}$—aldehyde (10% in DPG) | 5 |
| $C_{11}$—aldehyde (10% in DPG) | 5 |
|  | 900 |

By the addition of 100 parts of epoxide 8 there is produced here in a simple manner an attractive musk effect which confers fullness and warmth to the rose. By the addition of 100 parts of epoxide 7 the citronellol, which dominates too strongly in the original base, is enriched in an extraordinary manner. The base now becomes balanced.

H. Perfumery base with fruity character.

|  | Parts by weight |
|---|---|
| Ethyl 3-methyl-3-phenyl-glycidate | 50 |
| Ethyl acetoacetate | 15 |
| Dimethyl-benzyl butyrate | 15 |
| Maltyl isobutyrate | 10 |
| Benzyl acetate | 10 |
| Ethyl acetate | 5 |
| Lemon oil | 5 |
| Dipropylene glycol | 795 |
|  | 900 |

The addition of 100 parts of epoxide 8 to this generally fruity base produces an interesting effect in the direction of stone fruit. On the other hand, with 100 parts of epoxide 7 there results in a very simple manner a very fine raspberry note.

J. Perfumery base in the direction of tulip.

|  | Parts by weight |
|---|---|
| Phenylethyl alcohol | 100 |
| Myraldylacetat TM [[4-(4-methyl-3-pentenyl)-3-cyclohexen-1-yl]methyl acetate] | 100 |
| Methyl dihydrojasmonate | 100 |
| Acetal CD (glycerine acetal of phenylacetaldehyde) | 100 |
| Hydroxycitronellal | 160 |
| Farnesol | 40 |
| Hexyl salicylate | 30 |
| Terpineol | 30 |
| Cyclamen aldehyde | 20 |
| Linalool | 20 |
| Linalyl anthranilate | 10 |
| Amyl salicylate | 10 |
| C$_{11}$—aldehyde (10% in DPG) | 10 |
| Benzyl acetate | 8 |
| Hexenyl benzoate | 8 |
| Hexenyl acetate (10% in DPG) | 8 |
| p-Cresyl isobutyrate (10% in DPG) | 6 |
| Indole (10% in DPG) | 6 |
| Syringaaldehyde | 4 |
| Dimethyl acetal hydratropaldehyde (10% in DPG) | 30 |
| DPG | 100 |
|  | 900 |

The addition of 100 parts of epoxide 8 confers a musk character in the direction of ethylene brassilate to this flowery base.

We claim:
1. A compound of the formula

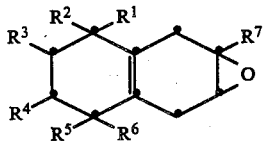

wherein:
$R^1$, $R^2$, $R^5$ and $R^6$ represent methyl, and
$R^3$, $R^4$ and $R^7$ represent hydrogen or methyl.

2. A compound according to claim 1 wherein $R^3$ and $R^7$ are methyl and $R^4$ is hydrogen, said compound identified as 6,7-epoxy-1,1,3,4,4,6-hexamethyl-1,2,3,4,5,6,7,8-octahydronaphthalene.

3. A compound according to claim 1 wherein $R^7$ is methyl and $R^3$ and $R^4$ are hydrogen, said compound identified as 6,7-epoxy-1,1,4,4,6-pentamethyl-1,2,3,4,5,6,7,8-octahydronaphthalene.

4. A compound which is selected from the group consisting of 6,7-epoxy-1,1,4,4tetramethyl-1,2,3,4,5,6,7,8-octahydronaphthalene, 6,7-epoxy-1,1,3,4,4-pentamethyl-1,2,3,4,5,6,7,8-octahydronaphthalene, 6,7-epoxy-1-ethyl-1,4,4,6-tetramethyl-1,2,3,4,5,6,7,8-octahydronaphthalene, 6,7-epoxy-1-isopropyl-4,4,7-trimethyl-1,2,3,4,5,6,7,8-octahydronaphthalene and 6,7-epoxy-1-ethyl-1,4,4,7-tetramethyl-1,2,3,4,5,6,7,8-octahydronaphthalene.

5. A compound of the formula

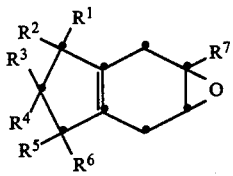

wherein:
$R^1$, $R^2$, $R^5$ and $R^6$ represent methyl, and
$R^3$, $R^4$ and $R^7$ represent hydrogen or methyl.

6. A compound according to claim 5 wherein $R^3$ is methyl and $R^4$ and $R^7$ are hydrogen, said compound identified as 5,6-epoxy-1,1,2,3,3-pentamethyl-4,5,6,7-tetrahydroindane.

7. A compound which is selected from the group consisting of 5,6-epoxy-1,1,3,3,5-pentamethyl-4,5,6,7-tetrahydroindane, 5,6-epoxy-1,1,2,3,3,5-hexamethyl-4,5,6,7-tetrahydroindane, 5,6-epoxy-3-ethyl-1,1,3,5-tetramethyl-4,5,6,7-tetrahydro-indane, 5,6-epoxy-1-isopropyl-2,3,3,5-tetramethyl-4,5,6,7-tetrahydroindane, 5,6-epoxy-1-isopropyl-2,2,3,3,5-pentamethyl-4,5,6,7-tetrahydroindane, and 5,6-epoxy-3-ethyl-1,1,3-trimethyl-4,5,6,7-tetrahydroindane.

8. A fragrance composition comprising an olfactorily effective amount of a compound of the formula

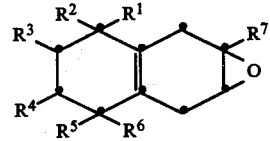

wherein:
$R^1$, $R^2$, $R^5$ and $R^6$ represent methyl, and
$R^3$, $R^4$ and $R^7$ represent hydrogen or methyl
and at least one other olfactory agent.

9. A composition according to claim 9 wherein $R^3$ and $R^7$ are methyl and $R^4$ is hydrogen, said compound identified as 6,7-epoxy-1,1,3,4,4,6-hexamethyl-1,2,3,4,5,6,7,8-octahydronaphthalene.

10. A composition according to claim 8 wherein $R^7$ is methyl and $R^3$ and $R^4$ are hydrogen, said compound identified as 6,7-epoxy-1,1,4,4,6-pentamethyl-1,2,3,4,5,6,7,8-octahydronaphthalene.

11. A fragrance composition comprising an olfactorily effective amount of a compound of the formula

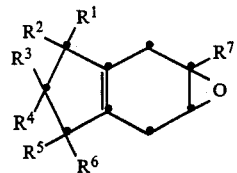

wherein:

$R^1$, $R^2$, $R^5$ and $R^6$ represent methyl, and $R^3$, $R^4$ and $R^7$ represent hydrogen or methyl, and at least one other olfactory agent.

12. A composition according to claim 11 wherein $R^3$ is methyl and $R^4$ and $R^7$ are hydrogen, said compound identified as 5,6-epoxy-1,1,2,3,3-pentamethyl-4,5,6,7-tetrahydroindane.

13. A flavor composition comprising an effective amount of a compound of the formula

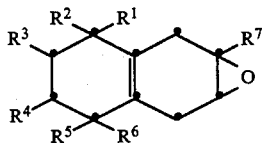

wherein:

$R^1$, $R^2$, $R^5$ and $R^6$ represent methyl and $R^3$, $R^4$ and $R^7$ represent hydrogen or methyl, and at least one other flavoring agent.

14. A composition according to claim 13 wherein $R^3$ and $R^7$ are methyl and $R^4$ is hydrogen, said compound identified as 6,7-epoxy-1,1,3,4,4,6-hexamethyl-1,2,3,4,5,6,7,8-octahydronaphthalene.

15. A composition according to claim 13 wherein $R^7$ is methyl and $R^3$ and $R^4$ are hydrogen, said compound identified as 6,7-epoxy-1,1,4,4,6-pentamethyl-1,2,3,4,5,6,7,8-octahydronaphthalene.

16. A flavor composition comprising an effective amount of a compound of the formula

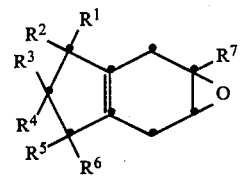

wherein:

$R^1$, $R^2$, $R^5$ and $R^6$ represent methyl and $R^3$, $R^4$ and $R^7$ represent hydrogen or methyl, and at least one other flavoring agent.

17. A composition according to claim 16 wherein $R^3$ is methyl and $R^4$ and $R^7$ are hydrogen, said compound identified as 5,6-epoxy-1,1,2,3,3-pentamethyl-4,5,6,7-tetrahydroindane.

* * * * *

UNITED STATES PATENT AND TRADEMARK OFFICE
CERTIFICATE OF CORRECTION

PATENT NO. : 4,634,548
DATED : January 6, 1987
INVENTOR(S) : Daniel Helmlinger et al.

It is certified that error appears in the above-identified patent and that said Letters Patent is hereby corrected as shown below:

In claim 9, column 20, line 58, correct "claim 9" to read --claim 8--.

Signed and Sealed this

Twenty-sixth Day of February, 1991

*Attest:*

HARRY F. MANBECK, JR.

*Attesting Officer*          *Commissioner of Patents and Trademarks*